United States Patent [19]
Kumagai

[11] Patent Number: 5,628,314
[45] Date of Patent: May 13, 1997

[54] MULTI-LASER BEAM-SCANNING THROUGH LIVING BODY PENETRATION DIAGNOSIS AND TREATMENT APPARATUS

[76] Inventor: Hiroaki Kumagai, 7-10, Minamitsukushino-4-chome, Machida-shi, Japan

[21] Appl. No.: 329,996

[22] Filed: Oct. 27, 1994

[30] Foreign Application Priority Data

Nov. 12, 1993 [JP] Japan .................................. 5-282981

[51] Int. Cl.$^6$ ..................................................... A61B 6/00
[52] U.S. Cl. ........................................ 128/653.1; 128/665
[58] Field of Search ................................. 128/653.1, 664, 128/665; 250/341.1; 356/432

[56] References Cited

U.S. PATENT DOCUMENTS

| | | | |
|---|---|---|---|
| 5,148,022 | 9/1992 | Kawaguchi et al. | 128/665 |
| 5,349,951 | 9/1994 | Ito et al. | 128/665 |

*Primary Examiner*—Ruth S. Smith
*Attorney, Agent, or Firm*—Oliff & Berridge

[57] ABSTRACT

In a diagnosis apparatus, a laser beam is radiated toward a living body, and this laser beam effects plane scanning in longitudinal and transverse directions of the living body, and the laser beam passed through the living body is received by a light-receiving detection plate. The laser beam radiation scanning device and the light-receiving detection plate are supported for rotation as a set, so that penetration images can be obtained in various directions without the need for moving the living body. If two sets of devices, each including the above laser beam radiation scanning device and the above light-receiving detection plate, are angularly spaced 90° from each other about the living body axis, a penetration data viewed from the front side of the living body, as well as penetration data viewed from the lateral side, can be obtained. Therefore, by processing these data by a computer, a colon endoscope or a catheter inserted into the living body can be graphically displayed as a stereoscopic penetration image on a television monitor. Further the two sets of the devices are located in various angular positions to obtain penetration images viewed in various directions so that an image of a focus obtained by contrast medium can be displayed on a television monitor by computer graphics. Further, using these devices, a diagnosis is made by a laser fluorescent penetration image of the living body or a fluorescent spectrophotometric pattern image, a laser treatment program and a spectrophotometric pattern recognition, thus effecting the diagnosis and the treatment simultaneously.

13 Claims, 8 Drawing Sheets

FIG. 14

MULTI-LASER BEAM-SCANNING THROUGH LIVING BODY PENETRATION DIAGNOSIS AND TREATMENT APPARATUS

BACKGROUND OF THE INVENTION

1. Field of the Invention

This invention relates to a diagnosis apparatus in which laser beams are applied to a living body, and a plane scanning is effected in a direction parallel to the axis of the living body and also in a direction perpendicular to this axis, and the laser beams passed through the living body are received by a light-receiving detection plate, and an image representative of the condition of the living body is displayed.

This invention also relates to a laser treatment apparatus in which laser beams are applied to a living body, and a plane scanning is effected in a direction parallel to the axis of the living body and also in a direction perpendicular to this axis, and the position and light amount of the laser beams passed through the living body are detected, and in accordance with these detected values, the laser beams of an intensity appropriate for the condition of the living body are applied to the living body.

2. Description of the Related Art

Images through a living body have heretofore been obtained mainly by x-ray fluoroscopy. In an x-ray fluoroscopy photographic diagnosis, an image of an affected part of a living body near to a film surface is clearly displayed on a scale close to the actual dimensions, but as the affected part is away from the film surface, the displayed image becomes increasingly unclear on a scale larger than the actual dimensions.

Generally, in a malignant tumor or the like, the boundary between the peripheral edge of such an affected part and the surrounding normal tissues is clear, and the affected part has an irregular contour, and has irregular projections and recesses at its peripheral edge. The density of the cells within the tumor is higher than that of normal tissues, and besides the nuclear-cytoplasmic ratio is higher. Therefore, generally, the degree of penetration through the tumor is lower than that of normal tissues, and besides the interior of the tumor tends to assume an uneven-pattern image. Generally, in the x-ray photography, the contour portion and interior of the affected part of the living body are made unclear by scattering components of the X-rays outside and inside the affected part, and in many cases the existence of the affected part is not detected until after the unevenness of the shade within the tumor becomes conspicuous. Particularly in soft internal organs, the difference in x-ray transmission rate between a tumor (affected part) and normal tissues is small, and it has been difficult to detect the tumor from the difference of the shadow before the tumor becomes considerably large and hard.

An x-ray fluoroscopic photography using a contrast medium is well known as a basic examination method for making an imaging diagnosis of an internal organ such as the stomach and the intestines. In this case, it is common to use one x-ray tube, and there is not a method in which fluoroscopic photographs of a living body are taken substantially simultaneously in different directions by the use of a plurality of x-ray tubes. Therefore, in order to obtain fluoroscopic images viewed in two directions, that is, from the front and the side of the internal organ, it is necessary to photograph the internal organ twice, changing the position of the body. At this time, the internal organs as well as the affected part are deformed in accordance with the change of the posture, and therefore this does not mean that the front image and side image thus photographed show the internal organ, as well as the affected part, in the same condition. Moreover, it is troublesome and time-consuming for an aged person and a physically-handicapped person to change the posture, and a longer time is required for photographic diagnosis.

Furthermore, since x-rays radiate in a conical configuration from one small tube, the exposed dose of the x-rays is not uniform over an entire area of a film surface, and therefore this is not suited for digital image processing although an analog image can be obtained easily. In addition to such uneven exposure, x-rays are affected by scattering components from other parts in the living body, and therefore an obtained image of the soft internal organs other than the bones becomes unclear, so that an imaging diagnosis could not be effected using such an unclear image. Namely, it has been almost impossible to effect a pseudo color image analysis and various image processing such as differential, integral, subtract and others diagnosis by the use of a fine gray image obtained by digitized data.

On the other hand, when a colon endoscope is to be inserted into the complicatedly-bent colon or when a catheter is to be inserted into a deep part of the body, it is necessary to effect an x-ray fluoroscopy to confirm the inserted condition. However, there is a risk that the patient to be examined, a doctor and an assistant participating in the examination are exposed to x-radiation, and therefore from a safety point of view, the x-ray fluoroscopy can not be carried out continuously, and generally the short-time x-ray fluoroscopy is repeated in the existing circumstances. Therefore, when inserting the endoscope or the catheter into a deep part, there are encountered a technical difficulty and a problem that the patient under examination suffers from a pain. Furthermore, in order to protect against radiation, a protective wall is provided, and a protector is put on the operator, and this increases the cost.

In the x-ray photographing of the luminal organs, such as the stomach and the intestines, and the blood vessels, a contrast medium is used. The contrast medium need to be of a nature hardly transmitting x-rays, and therefore it is limited to iodine and barium of high atomic number. An iodine contrast medium is injected into the luminal organ or the vascular organ, and is perfused, and x-ray fluoroscopy is carried out, and thereafter the iodine contrast medium tends to be absorbed into the body by diffusion. Although this has advantages, there is a risk that those patients who are hypersensitive to iodine suffer from a shock. Barium, which can not easily be absorbed biochemically and is liable to adhere to the wall of the digestive tract, has been frequently used as a contrast medium. However, barium can not be easily drunk, and can not easily be discharged out of the body, and in the case of obstinate constipation, there is often the risk of obstipation. Namely, the materials of the contrast medium which hardly transmit x-rays are limited, and besides the various problems remain unsolved, and because of the nature of the contrast medium, the nature of the image obtained by x-ray fluoroscopy has been limited to x-ray transmitting characteristics.

As a diagnosis method using other light than x-rays, there has been proposed a method of obtaining a penetration image using a laser beam. However, because of a transmission problem, this method has not yet been put into practical use for the penetration of the trunk portions where the flesh is thick and the bones exist. And besides, the laser beam has heretofore been radiated in a conical configuration from a rotating single laser beam source, and therefore this method suffers from some problems common to x-ray fluoroscopic photography.

SUMMARY OF THE INVENTION

It is an object of this invention to provide a penetration diagnosis apparatus which can overcome the problems with x-ray fluoroscopic photography by the use of other energy source than x-rays.

Another object of the invention is to provide a penetration diagnosis apparatus by which when an examination is carried out through an endoscope or a catheter by the use of a laser beam of a good linearity, a stereoscopic image of the interior of a living body can be continuously observed for a long period of time without exposing a doctor and an assistant to radiation energy.

A further object of the invention is to provide a penetration diagnosis apparatus which is capable of providing penetration images viewed in different directions without changing the position of a living body.

A still further object of the invention is to provide a penetration diagnosis apparatus which is capable of displaying a clear, high-resolution image of an affected part in a living body on an actual scale.

A further object of the invention is to provide a penetration diagnosis apparatus which is safe, and is capable of passing a laser beam of high energy through a living body without imparting any harmful effect to the cell tissues and tissue fluids of the living body.

A further object of the invention is to provide a penetration diagnosis apparatus in which a laser beam of an amount safe to a living body is radiated several times to that part of a living body to be examined within a certain time period, and a light-receiving device integrates the total light amount per unit radiation area, so that a clear image can be obtained without imparting any harmful effect to the living body.

A further object of the invention is to provide a penetration diagnosis apparatus which is capable of judging whether the patient under examination has a malignant tumor, an inflammation or a normal condition.

A further object of the invention is to provide a treatment apparatus which is capable of applying a laser beam of a predetermined light amount to a spot in accordance with the symptom of a living body to thereby effect a laser treatment of a tumor.

According to one aspect of the present invention, there is provided a laser beam-scanning living body penetration diagnosis apparatus comprising:

at least one set of laser beam parallel-scanning light-receiving detection mechanism comprising (i) at least one light source for emitting a laser beam, (ii) a device for radiating said laser beam toward a living body in a direction perpendicular to the axis of the living body, (iii) a device for moving the laser beam, directed toward the living body, in a direction parallel to the living body axis, (iv) a device for moving the laser beam, directed toward the living body, in a direction perpendicular to the living body, and (v) a detection plate for receiving the laser beam passed through the living body; and a device supporting said laser beam parallel-scanning light-receiving detection mechanism in such a manner that said mechanism is rotatable about the living body axis.

Two sets of laser beam parallel-scanning light-receiving detection mechanisms mentioned above are angularly spaced 90° from each other about the living body axis, and the living body is viewed in two directions, and this information obtained through the two detection plates is processed by a computer, and is graphically displayed. By doing so, a stereoscopic image of an endoscope or a catheter inserted into the living body can be obtained. Further these two sets of laser beam parallel-scanning light-receiving detection mechanisms are brought in various angular positions about the living body axis to obtain the penetration images viewed in various directions so that a focus in the living body under a certain condition, such as a condition as using a contrast medium, can be displayed as a stereoscopic image in a television monitor by computor graphics.

Preferably, a plurality of laser beams each one of which is of an intensity safe to the living body and is emitted from each one of a plurality of laser beam sources is formed into a group of highly concentrated laser beams, so that the light energy of high intensity, constituted by the laser beams closely spaced from one another, is radiated to the living body. By doing so, harmful effects on the cell tissues and tissue fluids of the living body can be reduced.

Preferably, the light-receiving detection plate comprises a photoelectronic array panel which is provided on a front surface of said detection plate facing the living body, and has a number of photoelectric units of a microscopic area arranged in a grid-like manner, a microprocessor array panel which is attached to a reverse surface of said photoelectronic array panel, and has a number of microprocessors arranged in a grid-like manner and connected respectively to said photoelectric units, and a semiconductor memory array panel which is attached to a reverse surface of said microprocessor array panel, and has a number of semiconductor memories arranged in a grid-like manner and connected respectively to said microprocessors, each of said photoelectric units being constituted by a number of microscopic photoelectric elements integrated and arranged in a plane. The laser beams each one of which is of intensity safe to the living body and which are densely gathered in a very small area, are radiated several times to that portion of the living body to be examined within a certain time period, and the total light amount received by the photoelectric unit is integrated, so that a clear penetration image of the living body can be obtained without imparting any harmful effect to the tissues of the living body. An ON-OFF switch is associated with each one of photoelectric units to be turned on only when the laser beams are radiated directly to the associated photoelectric unit, so that a penetration image of a high resolution can be obtained.

If a tumor fluorescent agent which is highly concentrated is administered to the patient for a certain time period, the fluorescent material collects at a tumor, and therefore when a laser penetration scanning is carried out, it is observed that the tumor emits fluorescent light. At this time, several fluorescent wavelength filters, respectively transmitting different fluorescent wavelengths within a certain wavelength band, are sequentially inserted to be disposed above the front surface of the photoelectronic array panel, so that a characteristic curve representing the relation between the fluorescent intensity and the wavelength of the passed fluorescence received by the photoelectric unit is obtained. This characteristic curve is compared with a pre-measured characteristic curve, and by doing so, it can be judged from a pseudo color image whether the penetrated part has a malignant tumor, an inflammation or a normal condition.

Further, in the present invention, it is detected which photoelectronic unit of the photoelectric array panel is receiving the laser beam, and the amount of this radiated light is detected, and this detected value is compared with a laser beam amount suitable for the treatment of a predetermined symptom, and the laser beam source is controlled. By doing so, the laser treatment can be carried out.

Further, in combination with the above symptom judging device, the above treatment apparatus can effect a laser treatment in accordance with the symptom of the patient.

Other objects, construction and advantageous effects of the present invention will become manifest from the following description of the preferred embodiments and the accompanying drawings.

DESCRIPTION OF THE PREFERRED EMBODIMENTS

Figure 1:
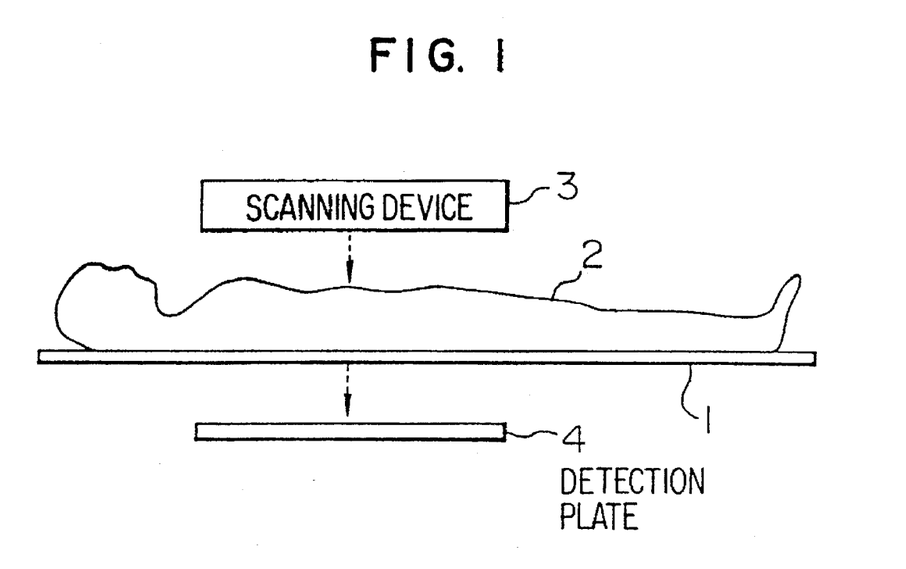
FIG. 1 is a side-elevational view schematically showing the principle of a laser beam parallel-scanning light-receiving detection mechanism of the invention.
Figure 2:
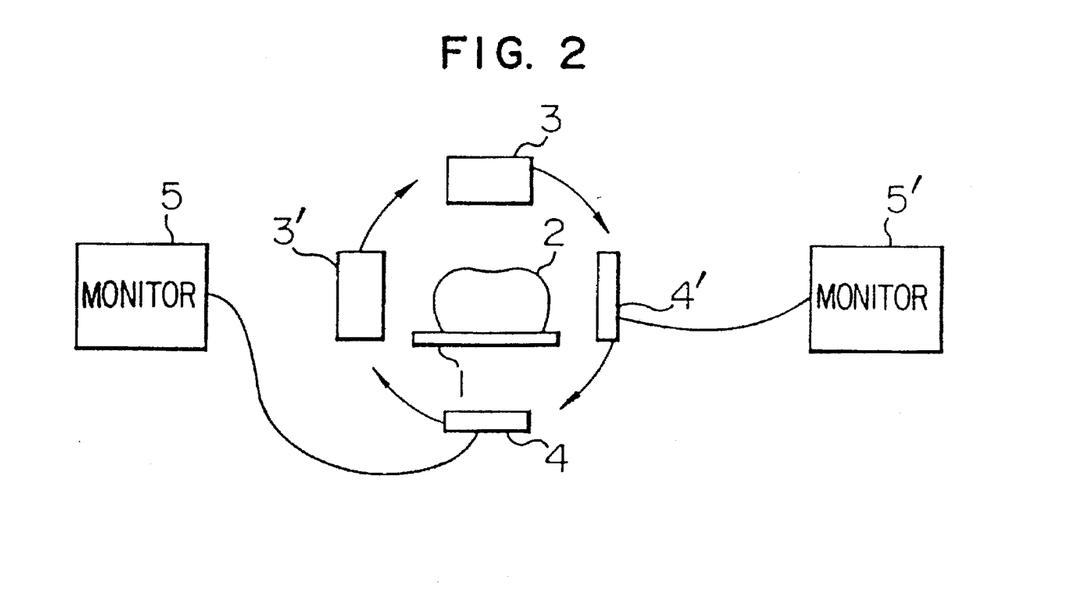
FIG. 2 is a transverse cross-sectional view schematically showing a construction in which two sets of laser beam parallel-scanning light-receiving detection mechanisms of FIG. 1 are used.

FIG. 1 is a schematic side-elevational view of a laser beam parallel-scanning light-receiving detection mechanism of a laser beam-scanning living body penetration diagnosis apparatus of the present invention, and FIG. 2 is a schematic transverse cross-sectional view of this mechanism.

As shown in FIG. 1, the laser beam parallel-scanning light-receiving detection mechanism comprises a laser beam parallel-radiating scanning device 3 disposed above a living body 2 laid down on a bed 1, and a light-receiving detection plate 4 disposed below the living body 2. Thus, the living body 2 is interposed between the scanning device 3 and the detection plate 4. As will more fully be described later, the laser beam parallel-radiating device 3 radiates a laser beam, emitted from a laser beam source, toward the living body 2, and also moves this laser beam in a longitudinal direction parallel to the center axis (hereinafter referred to as "living body axis") of the living body 2 and also in a transverse direction perpendicular to the living body axis, thereby effecting parallel scanning over an entire area of that part of the living body to be examined. The parallel-scanning laser beam passed through the living body is received by the light-receiving detection plate 4.

Figure 3:
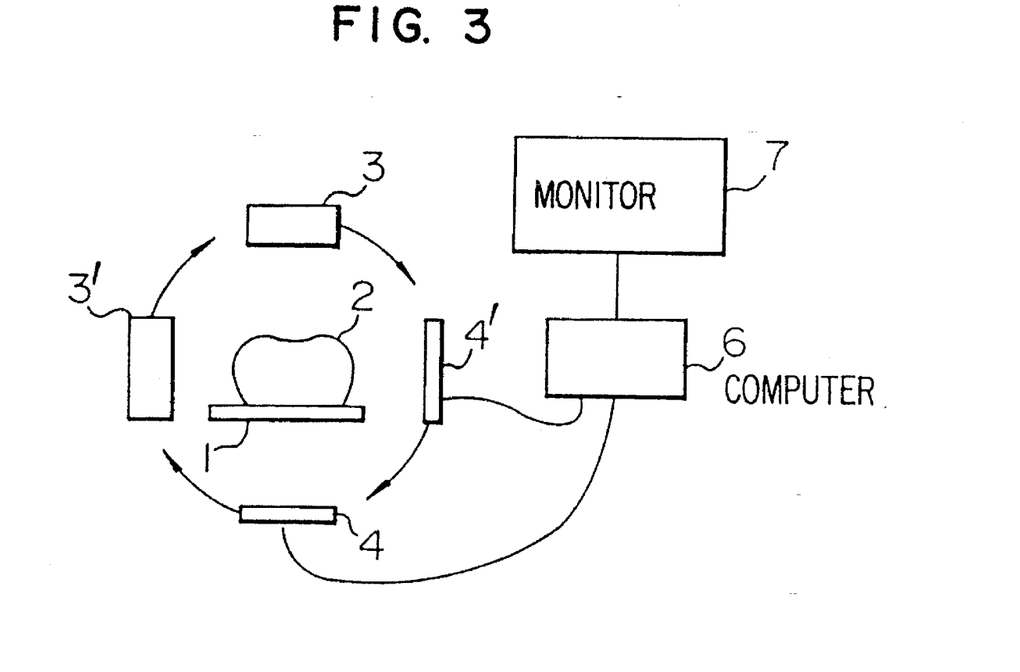
FIG. 3 is a schematic view of an apparatus for graphically displaying a stereoscopic penetration image, using the apparatus of FIG. 2.

As shown in FIG. 2, the laser beam parallel-scanning light-receiving detection mechanism, having the laser beam parallel-radiating device 3 and the light-receiving detection plate 4 as a set, is supported for rotation about the living body 2, and the laser beam parallel-radiating device 3 is rotated to a desired angular position to obtain penetration data representative of an image of the living body 2 viewed in a desired direction while the living body 2 remains stationary or laid on the bed 1. Thus, the position or posture of the living body 2 does not need to be changed. Further, if another laser beam parallel-scanning light-receiving detection mechanism (see FIG. 2), comprising a laser beam parallel-radiating device 3' and a light-receiving detection plate 4', is provided in suitably angularly spaced relation to the first-mentioned laser beam parallel-scanning light-receiving detection mechanism, the penetration data representative of images viewed in two different directions can be obtained substantially simultaneously. The data, obtained respectively at the light-receiving detection plates 4 and 4', are sent as electrical signals directly to television monitors 5 and 5', respectively, where these data are displayed as penetration images of different directions, respectively. As shown in FIG. 3, if the laser beam parallel plane-scanning is effected in such a manner that the two sets of laser beam parallel-scanning light-receiving detection mechanisms are angularly spaced 90° such that the laser beam parallel-radiating device 3 is disposed above the living body 2 while the laser beam parallel-radiating device 3' is disposed in opposed relation to the side of the living body 2, the penetration data, viewed from the upper side and lateral side of the living body 2, can be obtained at the light-receiving detection plates 4 and 4', respectively. These data are inputted as electrical signals to a computer 6, and are processed by it, so that a stereoscopic image of a colon endscope or a catheter inserted into the living body can be displayed on a television monitor so as to facilitate the deep insertion and the inspection thereof. Further these two sets of laser beam parallel-scanning light-receiving detection mechanisms 3 are brought in various angular positions about the living body axis to obtain the penetration images viewed in various directions so that a focus in the living body 2 under a certain condition, such as a condition as using a contrast medium, can be displayed as a stereoscopic image in a television monitor by computer graphics. More than two sets of laser beam parallel-scanning light-receiving detection mechanisms may be provided if necessary. By thus providing not less than two sets of laser beam parallel-scanning light-receiving detection mechanisms, the shape and position of a colon endoscope or a catheter inserted into the living body can also be displayed on the television monitor 7 in a stereoscopic manner, and therefore such an instrument can be safely inserted deep into the living body while confirming its position.

If illumination radiation for the inspection of the internal organ of the living body by an endoscope is carried out simultaneously with the laser beam radiation, they interfere with each other, so that it is difficult to obtain a clear image. Therefore, it is necessary to effect time-sharing in such a manner that the two radiation times alternate. Similarly, where the plurality of laser beam parallel-scanning light-receiving detection mechanisms are used to obtain the penetration data representative of the images viewed in the plurality of different direction, it is necessary to effect time-sharing so that the laser beams emitted from the respective laser beam parallel-radiating devices will not collide with one another in the living body. These time-sharings can be achieved by effecting the ON-OFF control of the plurality of light sources so that the plurality of laser beams, emitted respectively from these light sources, can be alternately radiated discontinuously, but time-sharing can also be achieved using other suitable optical device.

Figure 4:
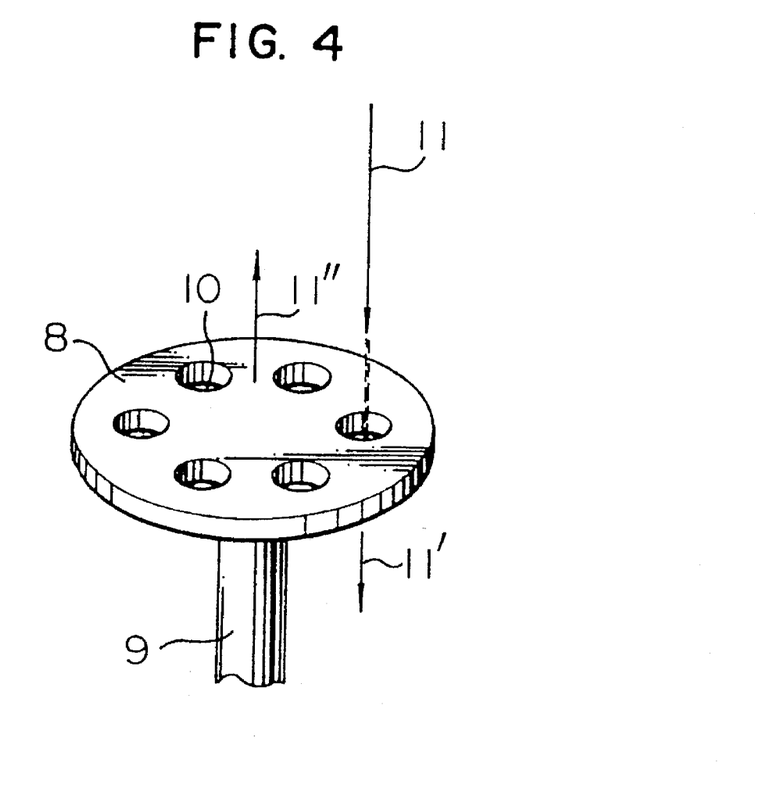
FIG. 4 is a perspective view of one embodiment of a device for forming two time-shared laser beams from a single laser beam, the two time-shared laser beams being fed respectively to two sets of laser beam parallel-scanning light-receiving detection mechanisms.

FIG. 4 shows one such example. A disk 8 rotates about an axis of a shaft 9, and a plurality of holes 10 are formed through the disk 8, and are arranged on a circle. An upper surface of the disk 8 is formed into a mirror surface. A laser beam 11, emitted from a single laser beam source, is directed toward a given point on the circle on which the through holes 10 are arranged. When one of the through holes 10 in the rotating disk 8 comes right beneath the laser beam 11, the laser beam passes through this through hole 10 to form a downwardly-directed laser beam 11'. When that portion of the disc 8 lying between the two adjacent through holes 10 comes beneath the laser beam 11, the laser beam 11 is reflected to form an upwardly-directed laser beam 11". Thus, the single laser beam 11 is converted into the two time-shared, discontinuous laser beams 11' and 11". These laser beams 11' and 11" are used in such a manner that they are radiated from the two laser beam parallel-radiating devices 3 and 3', respectively.

Figure 5:
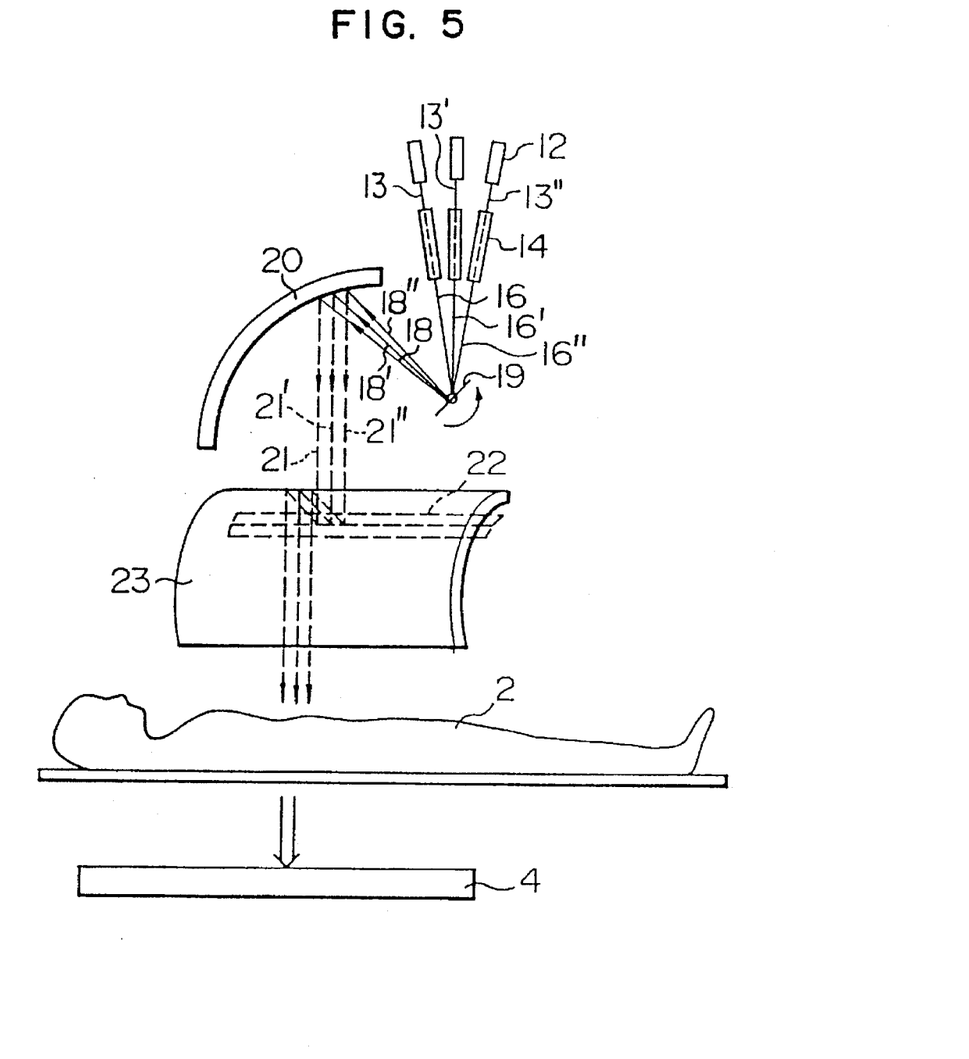
FIG. 5 is a schematic view of an apparatus in which a plurality of laser beams emitted from a plurality of laser beam sources are formed into a bundle-like group of parallel laser beams, and are applied to a living body while scanning in longitudinal and transverse directions of the living body.
Figure 6A:
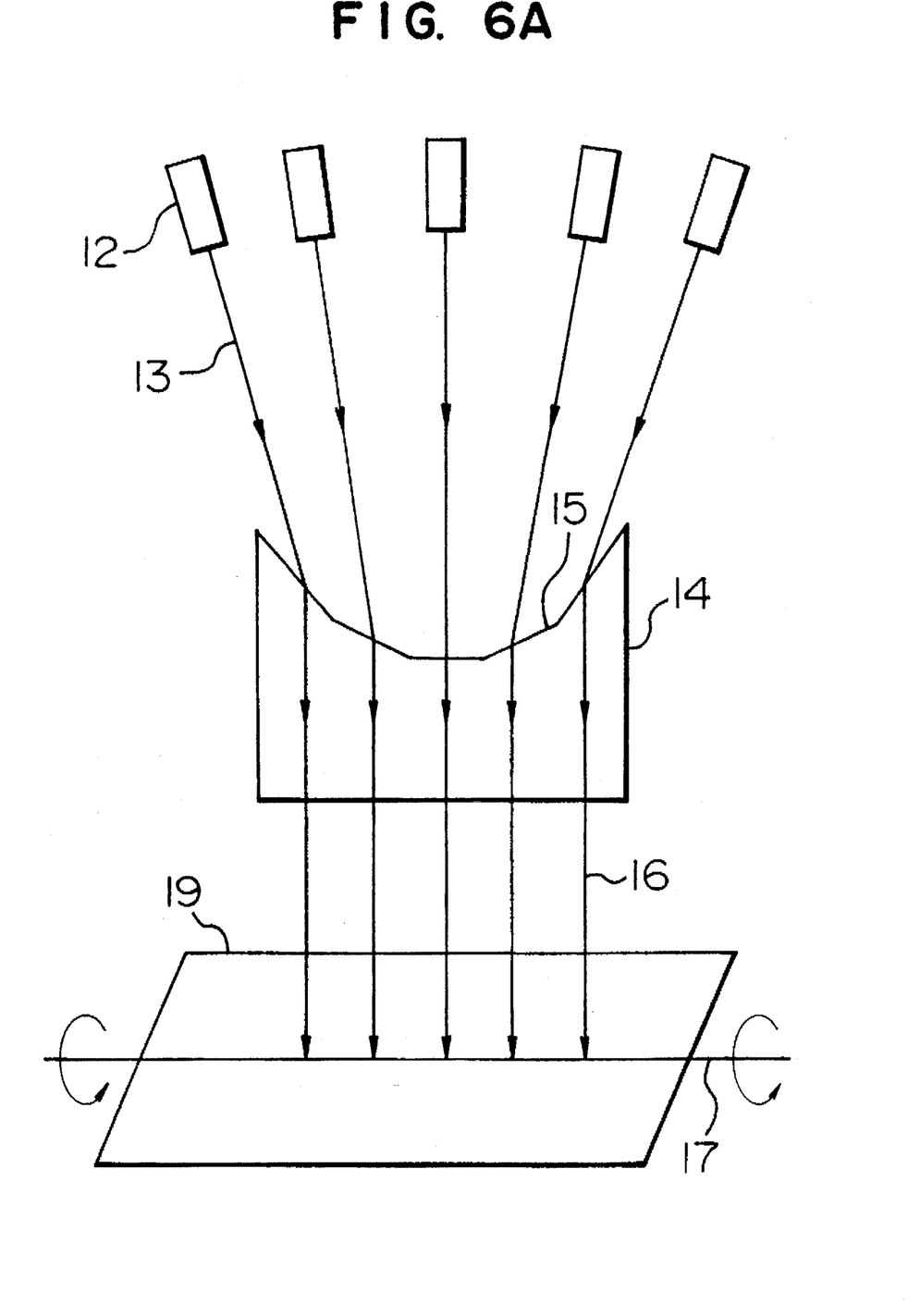
FIG. 6A is a schematic view showing an optical prism system in which in the embodiment of FIG. 5, laser beams emitted from a plurality of laser beam sources in one row are formed into a plurality of parallel laser beams, and are cast along an axis of rotation of a rotary mirror.

FIG. 5 shows one embodiment of a laser beam parallel-radiating scanning device. In this embodiment, there are provided a plurality of laser beam sources 12 arranged in a plurality of rows (for example, three rows as shown in this figure). As shown in FIG. 6A, each row includes a plurality of laser beam sources 12 (for example, five laser beam sources) disposed in spaced relation to emit a plurality of laser beams in various directions to convert in a plane. The plurality of laser beams 13 emitted from the associated sources 12 in each row are cast onto a prism 14. The upper surface 15 of the prism 14 is composed of five plain sections extending at different angles, each section receiving each one of laser beams, so that the plurality of laser beams 13 received by the prism 14 at different incident angles are refracted to the form a plurality of parallel laser beams 16. The parallel laser beams 16 are cast on an upper rotary mirror 19 along an axis 17 of rotation thereof and reflected toward an upper parabolic concave mirror 20 (in FIG. 5). In like manner, a plurality of laser beams 13' or 13" emitted from a plurality of laser beam sources in each one of the other two rows are refracted through a prism 14 to form a plurality of parallel laser beams 16' or 16" which are cast on the upper rotary mirror 19 along the axis 17 of rotation thereof and reflected toward the upper parabolic concave mirror 20.

Figure 6B:
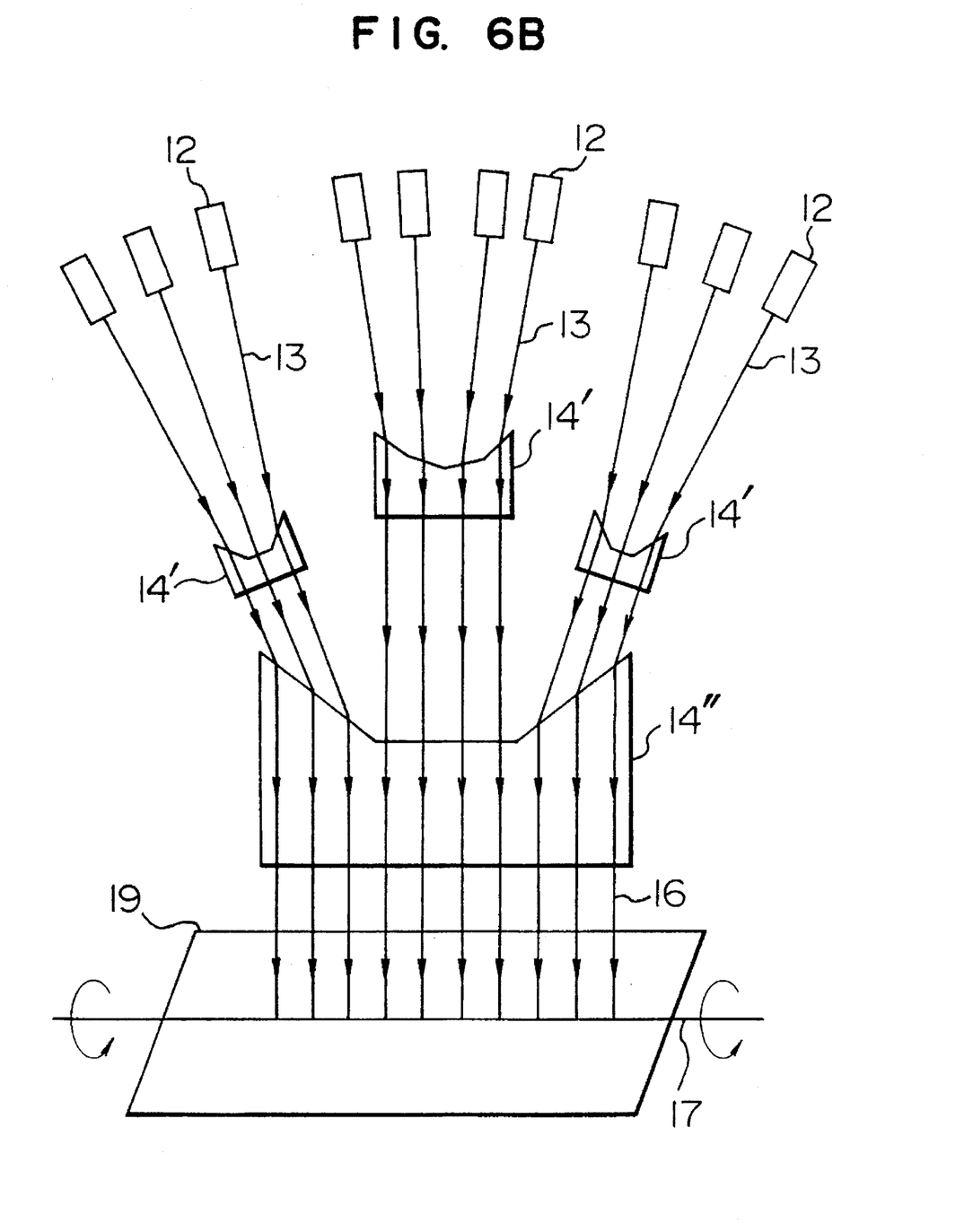
FIG. 6B is a schematic view showing another optical prism system in which the system of FIG. 6A is modified such that a larger number of parallel laser beams are cast along an axis of rotation of a rotary mirror.

FIG. 6B shows a parallel laser beam forming system modified from the system of FIG. 6A such that a larger number of parallel laser beams are formed. In FIG. 6B, ten laser beam sources 12 are provided in a row and are separated into a central group including four sources and left and right groups each including three sources. The system is composed of three upper prisms 14' and one lower prism 14". Four laser beams 13 emitted from laser beam source 12 in the central group are formed into four parallel laser beams in vertical direction through the central upper prism 14', while three laser beams 13 emitted from three laser beam sources 12 in each one of left and right groups are formed into three parallel laser beams in inclined direction. The lower prism 14" has an upper surface divided into a central horizontal section on which four parallel laser beams passing through the upper central prism 14' are cast and left and right slant sections on each one of which three inclined parallel laser beams passing through the associated left or right prism 14' are cast, whereby the lower prism 14" serves to form all of incident laser beams into ten parallel laser beams all in vertical directions. In the like manner as explained as to FIG. 6A, these vertical parallel laser beams are cast on the upper rotary mirror 19 along the axis of rotation thereof. In FIGS. 6A and 6B, although they are exaggerated for the sake of clarity, it is to be understood that the parallel laser beams are spaced at an equal microscopic distance, so far as interference and deflection between mutual parallel laser beams do not effect. It is also to be understood that the number of laser beam sources is not limited to those as described above but may be changed in the number of rows and in the number in each row. A part of component of the laser beam is reflected at the upper surface of the prism 14, 14' or 14" and this reflected component is removed by a light trap.

One of all laser beams cast on the upper rotary mirror 19, preferably the laser beam located at the center of a bundle of all laser beams, is periodically cut for a microscopic time by inputting pulse signals, to serve as a marker for detecting the coordinate of position of a part of the living body which is being scanned by the bundle of laser beams, as described later.

With this arrangement, the three rows of laser beams are all cast on the living body in dense, parallel relation, and are moved parallel to effect the plane scanning, as later described. The laser beams, reflected by the upper rotary mirror 19, form three rows of parallel laser beams 18, 18' and 18", and are directed toward an upper parabolic concave mirror 20, as shown in FIG. 5. The axis of the upper rotary mirror 19 is disposed at the focus of the upper parabolic concave mirror 20 which has a parabolic internal surface, and extends in a direction perpendicular to the living body axis. The upper parabolic concave mirror 20 is in the form of a quarter of a hollow cylinder. The three rows of parallel laser beams 18, 18' and 18", reflected by the upper rotary mirror 19, impinge on the upper parabolic concave mirror 20, and are reflected by it to be converted into a group of downwardly-directed beams 21, 21' and 21". The group of beams 21, 21' and 21" move in a direction parallel to the living body axis in accordance with the rotation of the upper rotary mirror 19, and are applied to a lower rotary mirror 22. Similarly, the axis of the lower rotary mirror 22 is disposed at the focus of a lower parabolic concave mirror 23 which has a parabolic internal surface, and extends in a direction parallel to the living body axis. The lower parabolic concave mirror 23 is in the form of a quarter of a hollow cylinder. Therefore, the group of laser beams, reflected by the lower rotary mirror 22, are further reflected by the lower parabolic concave mirror 23 toward the living body 2, and are applied to the living body 2, and scan the living body 2 in a direction perpendicular to the living body axis in accordance with the rotation of the lower rotary mirror 22. Therefore, by rotating the upper rotary mirror 19 and the lower rotary mirror 22, that part of the living body to be viewed in a penetrating manner can be parallel scanned over an entire area thereof by the group of parallel laser beams (hereinafter referred to as "densely-gathered parallel laser beams") densely concentrated on a very small area. By thus applying the plurality of laser beams as one group to a very small region of the living body in a concentrated manner, the living body having a large thickness, as well as those parts of the living body (e.g. the bone) less liable to allow the beams to pass therethrough, can be viewed and detected in a penetrating manner. Additionally, the light energy of high intensity is not applied to one spot in a concentrated manner, but is dispersed over a given very small area, and therefore the cell tissues are prevented from being injured.

Each of the rotary mirrors 19 and 22 can reflect the laser beams toward the associated parabolic concave mirror 20, 23 only when the former is within a certain small rotation angle range. By utilizing this nature, the timings of respectively radiating the two laser beams can be shared where two sets of laser beam parallel-scanning light-receiving mechanisms are used. In this case, the rotations of the two upper rotary mirrors 19 are out of phase with each other, and while one of the upper rotary mirrors reflects the laser beams to the associated upper parabolic concave mirror 20, the other upper rotary mirror does not reflect the laser beams toward the associated upper parabolic concave mirror. By doing so, the time-sharing can be effected.

Figure 7:
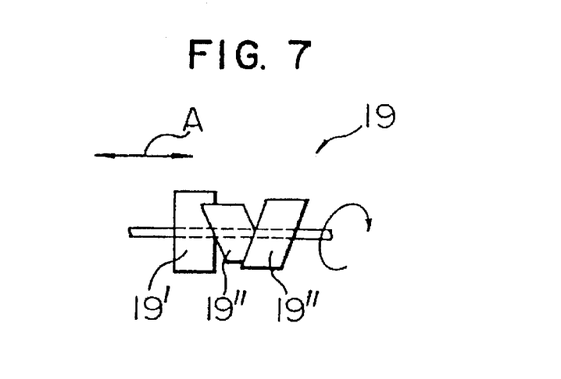
FIG. 7 is a perspective view of a modified rotary mirror used in the apparatus of FIG. 5.

FIG. 7 shows an embodiment in which the laser beams can be reflected toward the upper parabolic concave mirror 20 regardless of the phase of upper rotary mirror 19. In this embodiment, three rotary mirrors 19', 19" and 19''' are mounted on a rotation shaft for the upper rotary mirror 19 in such a manner that they are disposed, for example, 60° out of phase with one another. The rotation shaft, while being rotated, is reciprocally moved right and left as indicated by a double-headed arrow A. When the rotary mirror 19' comes out of an angle range in which this rotary mirror reflects the laser beams toward the upper parabolic concave mirror 20, the next rotary mirror 19" catches the laser beams, and reflects the same toward the upper parabolic concave mirror 20. Further, when the rotary mirror 19" becomes unable to achieve the predetermined reflecting operation, the rotary mirror 19''' is brought into a position where it receives the laser beams. When the rotary mirror 19''' ceases to effect the reflecting operation, the rotary mirror 19' again acts to perform the reflecting operation. Thus, during the rotation of the upper rotary mirrors 19, the laser beams can be always reflected toward the upper parabolic concave mirror 20. The number of the rotary mirrors, as well as the angular spacing of the rotary mirrors, can be suitably changed if necessary. The lower rotary mirror 22 can have the same construction, so that during the rotation, the laser beams can always be reflected toward the lower parabolic concave mirror 23.

Figure 8:
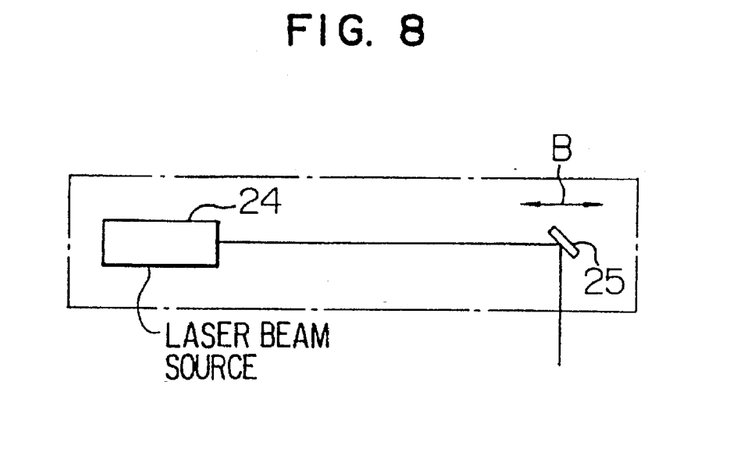
FIG. 8 is a schematic view of another embodiment of apparatus in which a laser beam, emitted horizontally from a laser beam source, is directed vertically, and is moved parallel to and along the length of the living body.

FIG. 8 shows another embodiment of the invention for effecting the scanning in the longitudinal direction of the living body as in the mechanism of FIG. 5 employing the upper rotary mirror 19 and the upper parabolic concave mirror 20 for moving the laser beams parallel to the living body axis. A laser beam is emitted from a laser beam source 24 in a direction parallel to the living body axis, and is directed downward by a reflecting mirror 25 inclined at an angle of 45° with respect to the emitted laser beam. The reflecting mirror 25, while kept inclined at 45°, is moved parallel to the living body axis as indicated by arrow B, thereby moving the downwardly-directed laser beam in the longitudinal direction of the living body. As a mechanism for scanningly moving the downwardly-directed laser beam in the transverse direction of the living body, a mechanism, comprising the lower rotary mirror 22 and the lower parabolic concave mirror 23 shown in FIG. 5, may be used, or any other suitable mechanism may be used.

Figure 9:
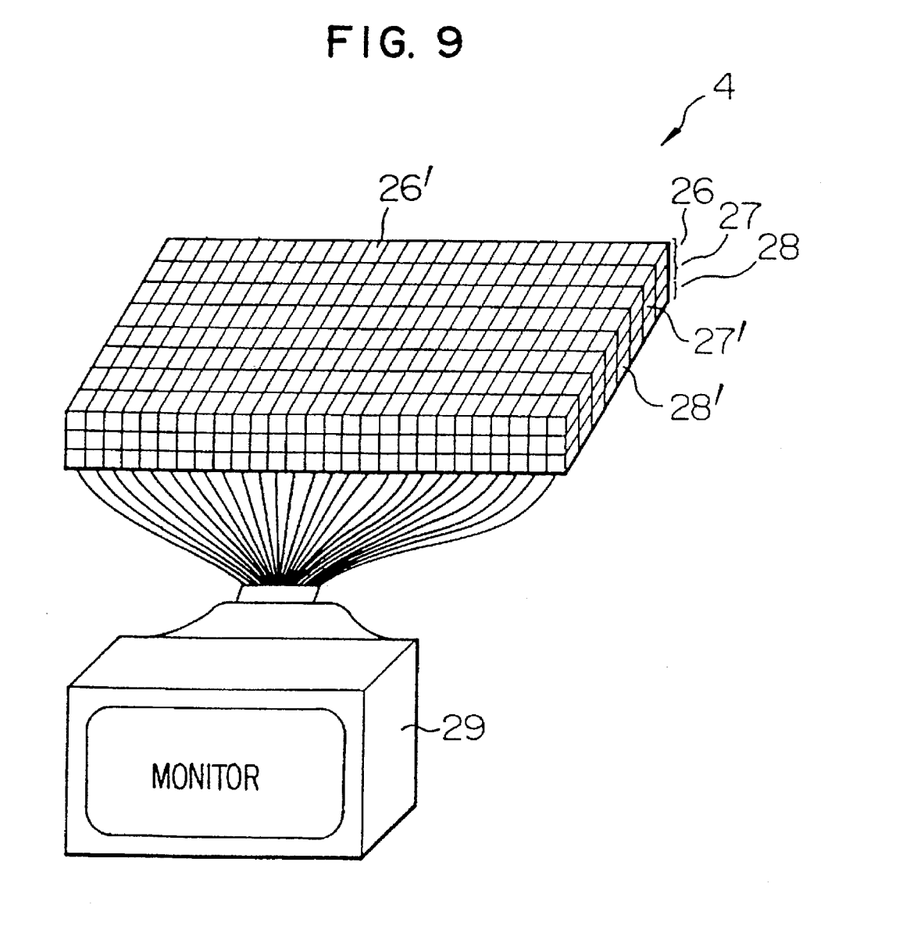
FIG. 9 is a schematic, perspective view of a preferred embodiment of a laser beam receiving detection plate used in combination with the laser beam parallel-scanning radiation apparatus of FIG. 5.

FIG. 9 shows an embodiment of a light-receiving detection plate 4 used in combination with the laser beam group parallel-scanning radiating device of FIG. 5. This light-receiving detection plate comprises a photoelectronic array panel 26, a microprocessor array panel 27, and a semiconductor memory panel 28 which are superposed in this order from the top to provide a three-layer construction. The photoelectronic array panel comprises a number of photoelectric units 26' of a microscopic area arranged in a grid-like manner. Each of the photoelectric units 26' is constituted by a number of microscopic photoelectric elements integrated and arranged in a plane, and usually has an area capable of receiving the whole of a bundle (group) of highly concentrated laser beams radiated from the lower parabolic concave mirror 23 of FIG. 5. However, each photoelectric unit 26' may have such an area that several photoelectric units jointly receive the bundle group of laser beams. The microprocessor array panel 27 comprises a number of microprocessors 27' which are arranged in a grid-like manner, and are connected respectively to the photoelectric units 26'. The microprocessor array panel 27 performs computing processings in accordance with the total light amount of the laser beams received by the photoelectric units 26'. The semiconductor memory array panel 28 comprises a number of semiconductor memories 28' which are arranged in a grid-like manner, and are associated respectively with the microprocessors 27'. Each semiconductor memory 28' stores the data processed by the associated microprocessor 27', and also stores instructions required for the microprocessor 27'.

If the laser beams are applied directly to the light-receiving detection plate 4, with the living body not overlying the light-receiving detection plate 4, all of the photoelectric units need to receive a uniform laser beam amount. On the other hand, the position of the photoelectric unit to which the laser beams are to be radiated is determined by the rotational positions of the upper and lower rotary mirrors 19 and 22 on which the marker laser beam, as described above, impinges. Therefore, the rotational positions of the two rotary mirrors 19 and 22 are inputted as electrical signals to the laser beam source, and also the microprocessor 27' performs a correction computation so that the light amount of the radiated laser beams received by the photoelectric unit 26' can be a reference value. This variation in light amount is mainly due to fluctuations in a power source of the laser beam source and a change of the total reduction of intensity of the laser beam caused by the optical circuit system including the prisms, the rotary mirrors and the parabolic concave mirrors intervening between the laser beam source and the photoelectric unit. The correction value calculated by the microprocessor is fed back to the laser beam source, and the energy of the laser beams to be radiated to the predetermined photoelectric unit is controlled.

For making a penetration diagnosis of the living body, a switch for each microprocessor is turned on only during the time when the each associated photoelectric unit 26' is scanned thereof, and in this manner all of the photoelectric units are scanned at least once. During the time when the patient holds his breath, and is stationary, all of the photoelectric units are scanned a plurality of times, and the total amount of light received by each photoelectric unit is integrated by the microprocessor and the semiconductor memory, and this is fed as an electrical signal to a television monitor 29, and is displayed on a cathode ray tube at a position corresponding to the photoelectric unit, and the whole of that part of the living body scanned for penetration purposes is displayed on the cathode ray tube as a gray image, or as a pseudo color image indicating the gray level difference.

Figure 10:
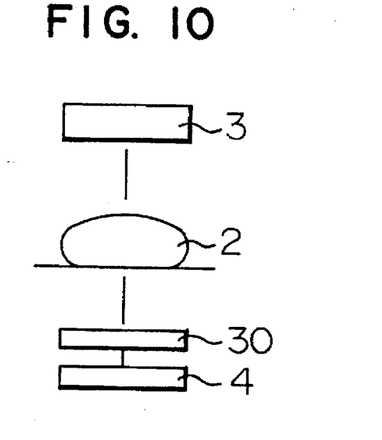
FIG. 10 is a schematic view showing a condition in which a laser exciting beam cut filter is inserted above the laser beam receiving detection plate of FIG. 9 in order to display a living body-penetration fluorescent image on a television monitor.

For obtaining a laser fluorescent image in order to make a diagnosis to determine whether or not any tumor exists or to make a diagnosis to determine the nature of a tumor, a laser exciting beam cut filter 30, corresponding to a fluorescent dye to be used, is inserted to be disposed above the light-receiving detection plate 4, as shown in FIG. 10, so that a living body-penetration fluorescent image can be displayed on the television monitor 29 (FIG. 9).

Figure 11:
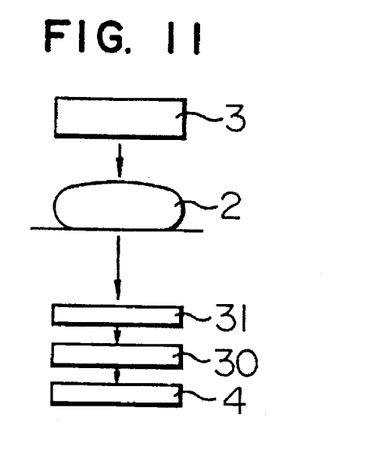
FIG. 11 is a schematic view showing a condition in which a fluorescent wavelength filter is further inserted above the laser exciting beam cut filter of FIG. 10 in order to obtain a laser fluorescent spectroscopic image so that the condition of the penetrated portion of the living body can be diagnosed.

For obtaining a laser fluorescence spectro-photometric image, a fluorescent wavelength filter 31 of various kinds, transmitting only a fluorescent component of a specified wavelength band, is further inserted to be disposed above the laser exciting beam cut filter 30, as shown in FIG. 11. If a fluorescent agent which is highly concentrated in the tumor is administered to the patient for a certain time period, the fluorescent agent collects at a tumor, and therefore when a laser penetration scanning is carried out, it is observed that the tumor emits fluorescent light. In this condition, several fluorescent wavelength filters 31, transmitting different fluorescent wavelengths, respectively, are prepared, and these filters are sequentially inserted to be disposed on the cut filter 30. The intensity of the fluorescent light passed through the fluorescent wavelength filter 31 is measured by the photoelectric units 26', so that a characteristic curve representing the relation between the wavelength of the passed fluorescent light and the intensity. This is compared with a characteristic curve beforehand measured, and by doing so, it can be judged from the spectrophotometric pattern whether the penetration spot has a malignant tumor, an inflammation or a normal condition. Thus judged penetration spots are plotted in different colors on the television monitor, so that a pseudo color image spectrophotometric pattern which is shown respectively as spots can be displayed on the cathode ray tube.

Figure 12:
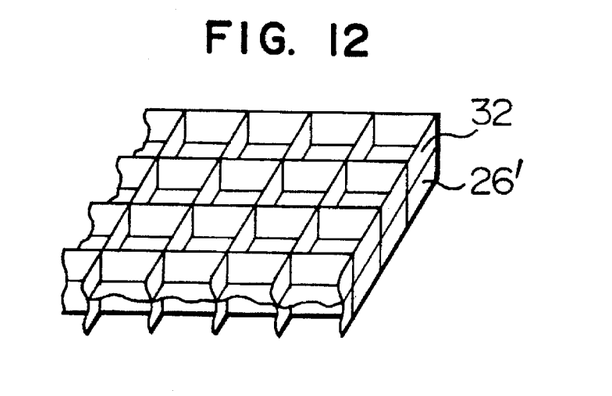
FIG. 12 is a fragmentary, perspective view of a light-deflecting grid plate mounted on a light-gathering electronic panel so that only linear components of the laser beam can be cast on electronic units of the laser beam receiving detection plate of FIG. 9.

The upper and lower parabolic concave mirrors 20 and 23 of the laser beam group parallel-scanning radiating device of FIG. 5 may be made smaller than the standard size if it is needed to compensate the reduction in the total amount of laser beams penetrating the living body caused by setting a light-deflecting grid plate and inserting various filters as described hereafter. By doing so, the scanning area by the group of the highly concentrated parallel laser beams can be reduced, so that the light amount per unit area of the living body (subjected to plane scanning) and per unit time can be increased, thereby compensating the reduction as described. In this case, a light-deflecting grid plate (see FIG. 12), constituted by a number of window frames 32 each having four vertical walls disposed respectively in registry with the four sides of the associated photoelectric unit 26', is mounted on the upper surface of the photoelectronic array panel 26 of FIG. 9, so that only linear components of the group of laser beams, radiated from the laser beam parallel-scanning radiating device 3 and passed through the living body, are received by the photoelectric units 26' whereas those light components, reflected and scattered in the living body, are removed. As a result, a laser beam penetration image of a high resolution can be obtained by the group of linear laser beams passed through the narrow portion of the living body.

Figure 13:
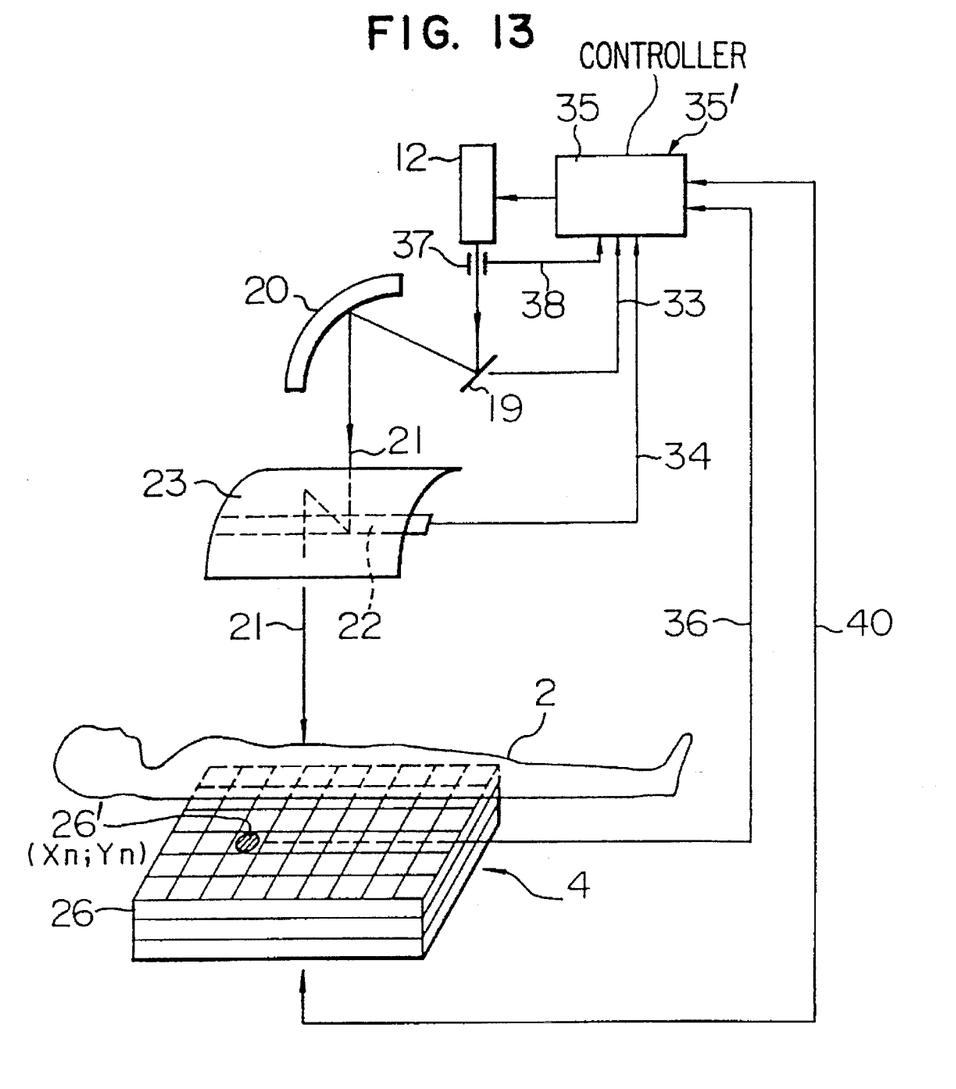
FIG. 13 is a schematic view of apparatus for effecting a laser treatment using the apparatus of FIG. 5.

FIG. 13 is a schematic view showing a condition in which a laser treatment is applied to an affected part of the living body, using the laser beam parallel-scanning radiating device of FIG. 5 and the light-receiving detection plate of FIG. 9. A laser beam 21, emitted from the laser beam source 12 and applied to the living body 2 via the prism 14, 14', 14", the upper rotary mirror 19, the upper parabolic concave mirror 20, the lower rotary mirror 22 and the lower parabolic concave mirror 23, pass through the living body 2, is cast on one of the photoelectric units 26' of the photoelectric array panel 26 at the uppermost layer of the light-receiving detection plate 4. As described above, two-dimensional coordinates ($x_n$, $y_n$) of the photoelectric unit 26' on which the laser beam is cast is determined by the rotational angular positions of the upper rotary mirror 19 and the lower rotary mirror 22. Therefore, these rotational angles are detected, and these detected values are converted into electrical signals representative of the x- and y-coordinates of the photoelectric unit 26' receiving the laser beam, and are inputted to a controller 35 for the laser beam source 12 via lines 33 and 34.

The light amount of the laser beam received by this photoelectric unit 26' is inputted to the controller 35 via a line 36, and in view of variations in the total reduction of intensity of the laser beam passing through the prisms 14, 14', 14", the upper rotary mirror 19, the upper parabolic concave mirror 20, the lower rotary mirror 22 and the lower parabolic concave mirror 23, a correction is made so that the amounts of light received respectively by all of the photoelectric units 26' can be made constant when the living body is not laid down, thereby controlling the laser output. Only one line 36 is shown in FIG. 13, and all of the photoelectric units 26' are connected to the line 36 so that the amount of light detected respectively by all of the photoelectric units 26' can be fed to the controller 35 via the line 36. In order that the laser can emit a predetermined output, a sensor 37 is provided beneath an outlet of the laser beam source, and the laser output detected by this sensor is fed back to the controller 35 via a line 38. Further, if the direction and situation of the laser beam emitted from the laser beam source are deviated from predetermined direction and situation due to the wavelength of the laser beam and the other reason, a control device is provided to detect the direction and situation of the beam and control the posture of the laser beam source in accordance with the detected value to emit the laser beam in the predetermined direction and situation. Although it has been described for illustration purposes that the above treatment apparatus uses the single laser beam, a group of highly concentrated parallel laser beams as described for FIGS. 5 to 9 are actually used. It will be readily appreciated that a similar output control can be effected with such a group of highly concentrated parallel laser beams. Only one of the photoelectric units 26' which is being scanned by the group of laser beams is turned on whereas the other photoelectric units are turned off. This ON-OFF control can be easily effected by using a device for detecting the x- and y-coordinates of the photoelectric units. In this manner, noise signals from those photoelectric units not subjected to the scanning are prevented from being inputted to the controller 35.

Figure 14:
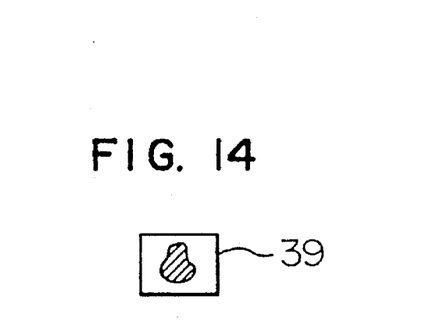
FIG. 14 is an illustration showing one example of a treatment graphic program used in the laser treatment apparatus of FIG. 13.

A treatment graphic program 39 (as shown in FIG. 14), representing the relation between the coordinates ($x_n$, $y_n$) of the photoelectric units and the laser output I ($x_n$, $y_n$) to be applied thereto, is beforehand inputted in the laser beam source controller 35. When the group of highly concentrated parallel laser beams effect parallel scanning the whole of the required part of the laid-down living body once to several times, the group of laser beams, passed through the living body to be reduced in intensity, are received by the photoelectric units 26', and the total light amounts thereof are computed by the semiconductor memory 28' and the microprocessor 27', and all of the computed values are fed to the laser beam source controller 35 via a line 40.

These detected coordinates of the photoelectric units and the total light amounts are displayed as images on the cathode ray tube, and at the same time are compared with the treatment graphic program stored in the laser beam source controller 35, and in accordance with this program, the laser output is controlled to be increased in an amount necessary for the treatment. This laser treatment method can be applied to a method of processing a product by a laser in which detected coordinates information and light amount information are compared with predetermined laser-processing reference instructions.

In the laser treatment apparatus of FIG. 13, a laser fluorescent spectrophotometric pattern can be displayed by inserting a fluorescent wavelength filter 31 (see FIG. 11) of various kinds to be disposed over the photoelectronic array panel 26. Therefore, by connecting this system to the laser beam source controller, a diagnosis and a treatment by the laser can be carried out simultaneously. Incidentally, by sequentially changing a laser wavelength by a dye laser (modulating wavelength laser) to obtain a plurality of spectrophotometric wavelength images, a laser fluorescent spectrophotometric image analysis treatment can be carried out.

In the present invention, not only barium and iodine but also a composite material composed of a material of combination of a dye (which flows in the internal organ in the living body, and is absorbed to cause metabolism in the internal organ) and any one of various intermediate metabolizing materials, such for example as a material of combination of yellow-green vegetable, liable to be absorbed from the digestive tract, and carbohydrates, can be used as a contrast medium. The condition in which the contrast medium is absorbed from the mucosa of the digestive tract and the condition in which the contrast medium moves to the various internal organs through the blood vessels and the lymph vessels can be observed. A diagnosis can be made using an abnormal perfusion distribution image for a malignant tumor or a tumefaction portion due to its lymphonodus metastasis. A diagnosis can be made using a fluorescent penetration image and a fluorescent spectro-photometric pattern image. A metabolism condition of the solid internal organ such as the liver and the kidney can be examined.

If two sets of laser beam parallel-scanning light-receiving detection mechanisms are spaced at the maximum angle from each other in such a manner that the two are not opposed to each other, and they are rotated sequentially to change the directions so that penetration images of the living body can be obtained from various directions, then the same number of the images can be obtained in about half of the time required for one set of laser beam parallel-scanning light-receiving detection mechanism to obtain the living body-penetration images from various directions. Therefore, the stereoscopic image of high quality can be easily obtained by computer graphics.

What is claimed is:

1. A laser beam-scanning living body penetration diagnosis apparatus comprising:
   a bed;
   at least one set of laser beam parallel-scanning light-receiving detection mechanisms comprising (i) a device disposed above said bed for radiating a bundle of parallel laser beams in a direction perpendicular to the axis of said bed, (ii) a device for moving said bundle of laser beams in a parallel direction to a longitudinal axis of the bed, (iii) a device for moving said bundle of laser beams in a direction perpendicular to the longitudinal axis of the bed, and (iv) a detection plate disposed below said bed for receiving said bundle of laser beams; and
   a device supporting said laser beam parallel-scanning light-receiving detection mechanisms in such a manner that said mechanisms are rotable about a fixed axis parallel to and upwardly spaced apart by a predetermined distance from the longitudinal axis of the bed.

2. Apparatus according to claim 1, in which said device for moving said bundle of laser beams in the direction parallel to the longitudinal axis of the bed comprises a first parabolic concave mirror in the form of a quarter of a hollow cylinder which has a parabolic internal surface, and extends above said bed in a direction perpendicular to the longitudinal axis of the bed, and a first rotary mirror which is located at the focus of said first parabolic concave mirror, is supported for rotation about a lateral axis extending perpendicular to the longitudinal axis of the bed, and receives said bundle of laser beams from said laser beam radiating device to reflect the laser beams to said first parabolic concave mirror;
   said device for moving said bundle of laser beams in the direction perpendicular to the longitudinal axis of the bed comprising a second parabolic concave mirror in the form of a quarter of a hollow cylinder which is disposed below said first parabolic concave mirror, and above said bed, has a parabolic internal surface, and extends in a direction perpendicular to said first parabolic concave mirror, and a second rotary mirror which is located at the focus of said second parabolic concave mirror, is supported for rotation about a longitudinal axis extending parallel to the longitudinal axis of the bed, and receives the laser beams from said first parabolic concave mirror to reflect the laser beams to said second parabolic concave mirror.

3. Apparatus according to claim 2, in which each of said first and second rotary mirrors comprises a rotation shaft reciprocally movable along an axis thereof, and a plurality of flat mirrors mounted on said rotation shaft and juxtaposed along said axis of said rotation shaft in such a manner that the angles of mounting of said flat mirrors are out of phase from one another.

4. Apparatus according to claim 1, in which said radiating device comprises a plurality of laser beam sources for emitting a plurality of laser beams and means for combining said plurality of laser beams into said bundle of parallel laser beams.

5. Apparatus according to claim 4, wherein said plurality of laser beam sources is arranged in a plurality of rows and said combining means comprises at least one prism having an upper surface receiving a plurality of laser beams emitted from a plurality of laser beam sources in each said row, said upper surface being formed in a shape to refract said plurality of laser beams to a plurality of vertically parallel laser beams.

6. Apparatus according to claim 5, wherein said plurality of laser beams emitted from said laser beam sources in each row is divided into plural groups, the apparatus further comprising a plurality of upper prisms, each receiving a plurality of laser beams in each said group for refracting said laser beams to a group of parallel laser beams and a lower prism receiving said plurality of groups of said parallel laser beams for issuing a plurality of vertically parallel laser beams in the number corresponding to the total number of laser beam sources in each row.

7. Apparatus according to claim 1, in which said light-receiving detection plate comprises a photoelectronic array panel which is provided on a front surface of said detection plate facing the living body, and a number of photoelectric units of a microscopic area arranged in a grid-like manner, a microprocessor array panel which is attached to a reverse surface of said photoelectronic array panel, and has a number of microprocessors arranged in a grid-like manner and connected respectively to said photoelectric units, and a semiconductor memory array panel which is attached to a reverse surface of said microprocessor array panel, and has a number of semiconductor memories arranged in a grid-like manner and connected respectively to said microprocessors, each of said photoelectric units being constituted by a number of microscopic photoelectric elements integrated and arranged in a plane.

8. Apparatus according to claim 7, in which a light-deflecting grid plate, constituted by window frames arranged in a grid-like manner, is mounted on said photoelectronic panel, each of said window frames having vertical walls extending upwardly from a periphery of the associated photoelectric unit.

9. Apparatus according to claim 7, in which said light-receiving detection plate further comprises a laser exciting beam cut filter disposed above said photoelectronic array panel, the apparatus further comprising a television monitor for displaying a living body-penetration fluorescent image in accordance with data obtained by said light-receiving detection plate.

10. Apparatus according to claim 1, in which at least two sets of said laser beam parallel-scanning light-receiving detection mechanisms are provided.

11. Apparatus according to claim 10, further comprising a device for effecting time sharing of two respective bundles of parallel laser beams of said two sets of laser beam parallel scanning light receiving detection mechanisms such that the operations of said two sets of laser beam parallel-scanning light-receiving detection mechanisms are prevented from interfering with each other.

12. A laser beam-scanning living body penetration diagnosis apparatus comprising:

a bed;

at least one set of laser beam parallel-scanning light-receiving detection mechanisms comprising (i) at least one laser beam source disposed above the bed for emitting a laser beam in a direction parallel to a longitudinal axis of the bed, (ii) a reflecting mirror disposed above said bed for reflecting said laser beam in a direction perpendicular to an axis of said bed, (iii) a device for moving said reflecting mirror parallel to and along the longitudinal axis of the bed, thereby moving the laser beam in a parallel direction to the longitudinal axis of the bed, (iv) a device for moving the laser beam in a direction perpendicular to the longitudinal axis of the bed, and (v) a detection plate disposed below said bed for receiving the laser beam; and a device supporting said laser beam parallel-scanning light receiving detection mechanisms in such a manner that the mechanisms are rotatable about a fixed axis parallel to and upwardly spaced apart by a predetermined distance from the longitudinal axis of the bed.

13. Apparatus according to claim 12, further comprising at least two sets of said laser beam parallel-scanning light-receiving detection mechanisms, and a device for effecting time-sharing of two respective laser beams of said two sets of laser beam parallel-scanning light-receiving detection mechanisms such that the operations of said two sets of laser beam parallel-scanning light-receiving detection mechanisms are prevented from interfering with each other.

* * * * *